(12) United States Patent
Adham et al.

(10) Patent No.: US 10,196,707 B2
(45) Date of Patent: Feb. 5, 2019

(54) PROCESS AND REACTOR FOR ARSENIC FIXATION

(71) Applicant: HATCH LTD., Mississauga (CA)

(72) Inventors: Kamal Adham, Toronto (CA); Christopher Thomas Harris, Linz (AT); Christopher Francis Michael Twigge-Molecey, Toronto (CA)

(73) Assignee: Hatch, LTD., Mississauga, ON (CA)

( * ) Notice: Subject to any disclaimer, the term of this patent is extended or adjusted under 35 U.S.C. 154(b) by 0 days.

(21) Appl. No.: 15/568,896

(22) PCT Filed: Apr. 12, 2016

(86) PCT No.: PCT/CA2016/050423
§ 371 (c)(1),
(2) Date: Oct. 24, 2017

(87) PCT Pub. No.: WO2016/168921
PCT Pub. Date: Oct. 27, 2016

(65) Prior Publication Data
US 2018/0105895 A1    Apr. 19, 2018

Related U.S. Application Data

(60) Provisional application No. 62/152,356, filed on Apr. 24, 2015.

(51) Int. Cl.
C22B 1/00    (2006.01)
C22B 1/11    (2006.01)
(Continued)

(52) U.S. Cl.
CPC ............ *C22B 1/11* (2013.01); *A61B 17/7098* (2013.01); *A61B 17/8095* (2013.01);
(Continued)

(58) Field of Classification Search
CPC ........ C22B 1/11; C01G 49/009; B01J 8/1845; B01J 8/1836; B01J 8/1827
(Continued)

(56) References Cited

U.S. PATENT DOCUMENTS 360,904 A * 4/1887 Parnell
921,645 A * 5/1909 Greenawalt
(Continued)

FOREIGN PATENT DOCUMENTS

CA    2824091 A1    4/2014

OTHER PUBLICATIONS

K. Adham et al, Two-Stage Fluid Bed Reactor for Arsenic Removal and Fixation, COM 2014—Conference of Metallurgists Proceedings, Jan. 1, 2014, 10 pages, published by the Canadian Institute of Mining, Metallurgy and Petroleum, Canada.
(Continued)

*Primary Examiner* — Steven J Bos
(74) *Attorney, Agent, or Firm* — Marshall & Melhorn, LLC.

(57) ABSTRACT

A process and reactor for arsenic fixation in which a first gas stream comprises oxygen and an iron-containing particulate material. The oxygen and particulate material may be fed to reactor through respective first and second inlets. A second gas stream containing one or more volatile arsenic compounds is fed through a third inlet and mixed with the first gas stream and the particulate material to produce a combined gas stream containing the volatile arsenic compounds and the particulate material. The arsenic compounds are reacted with iron in the particulate material as the combined gas stream flows through the reactor to produce solid iron arsenates which are then recovered. The portion of the reactor including the first, second and third inlets is verti-
(Continued)

cally oriented, and the reactor may include a venturi arrangement having a throat at which the second inlet is located.

18 Claims, 3 Drawing Sheets

(51) Int. Cl.
A61B 17/80 (2006.01)
A61B 17/70 (2006.01)
B01J 8/18 (2006.01)
C01G 49/00 (2006.01)
A61B 17/86 (2006.01)
A61B 17/56 (2006.01)
A61B 17/00 (2006.01)

(52) U.S. Cl.
CPC ........... *B01J 8/1827* (2013.01); *B01J 8/1836* (2013.01); *B01J 8/1845* (2013.01); *C01G 49/009* (2013.01); *A61B 17/864* (2013.01); *A61B 17/866* (2013.01); *A61B 17/8645* (2013.01); *A61B 2017/00884* (2013.01); *A61B 2017/00893* (2013.01); *A61B 2017/00955* (2013.01); *A61B 2017/561* (2013.01); *B01J 2208/00752* (2013.01); *B01J 2208/00893* (2013.01)

(58) Field of Classification Search
USPC .................................. 423/47, 87, 594.4, 602
See application file for complete search history.

(56) References Cited

U.S. PATENT DOCUMENTS

| | | | | |
|---|---|---|---|---|
| 1,075,011 A | * | 10/1913 | Christensen | C22B 3/10 266/178 |
| 1,718,825 A | | 6/1929 | Kirmse | |
| 2,056,564 A | * | 10/1936 | Carter | C22B 1/10 266/138 |
| 2,209,331 A | * | 7/1940 | Haglund | C22B 1/02 423/153 |
| 2,536,952 A | * | 1/1951 | McBean | C22B 1/10 241/19 |
| 2,596,580 A | * | 5/1952 | McKay | C22B 1/10 266/157 |
| 2,650,159 A | * | 8/1953 | Tarr, Jr. | C22B 1/10 266/172 |
| 2,867,529 A | * | 1/1959 | Forward | C22B 11/04 423/29 |
| 4,126,425 A | | 11/1978 | Twigge-Molecey | |
| 5,123,956 A | | 6/1992 | Fernandez et al. | |
| 6,248,301 B1 | * | 6/2001 | Hannaford | C22B 1/10 423/22 |
| 6,482,373 B1 | | 11/2002 | Hannaford et al. | |
| 6,656,722 B1 | | 12/2003 | Ruitenberg et al. | |
| 8,998,790 B2 | | 4/2015 | Lalancette et al. | |

OTHER PUBLICATIONS

Canadian Intellectual Property Office, The International Search Report and the Written Opinion issued in International application No. PCT/CA2016/050423, dated Jun. 15, 2016, 9 pages, Canadian Intellectual Property Office, Gatineau, Quebec, Canada.

* cited by examiner

PROCESS AND REACTOR FOR ARSENIC FIXATION

CROSS-REFERENCE TO RELATED APPLICATION

This application claims priority to and the benefit of U.S. Provisional Patent Application No. 62/152,356 filed Apr. 24, 2015, the contents of which are incorporated herein by reference.

FIELD

The present disclosure relates to fixation of arsenic from ores and concentrates into an environmentally stable form. In particular, the disclosure relates to an improved process and reactor for conversion of volatile arsenic compounds, such as arsenic oxides and/or sulfides, into stable iron arsenates.

BACKGROUND

The production of gold, copper and nickel increasingly relies on the treatment of ore bodies which contain significant quantities of arsenic-bearing minerals. In some cases, the ores and concentrates recovered from these ore bodies contain levels of arsenic which are too high to be accepted by most smelters, and therefore arsenic must typically be removed prior to smelting. Also, arsenic in many gold ores must be removed in order to prevent gold encapsulation by iron arsenates during the oxidative roast used to remove sulfur and organic carbon from refractory ores.

Arsenic removal is typically carried out by subjecting an arsenic-bearing ore or concentrate to a neutral or partial roast in a fluid bed or multi-hearth roaster, resulting in the conversion of arsenic to a gaseous oxide and/or sulfide. These gaseous arsenic compounds are collected in the off-gas system and stabilized in various forms.

After its removal from the ore or concentrate, fixation of the arsenic into a stable form is critical due to the serious environmental and health issues that arsenic contamination can cause. As disclosed in U.S. Pat. No. 4,126,425, arsenic can be recovered as solid arsenic oxide through sublimation of gaseous arsenic oxide from roaster off-gases. However, due to the poor environmental stability of arsenic oxide and its limited market, it is desirable to fix the arsenic in a more stable form.

There are several disadvantages of conventional processes for arsenic fixation. For example, fixation of arsenic as a stable, crystalline arsenate such as scorodite typically requires expensive oxidation reagents and the need for high pressure autoclaves. Other options, such as the formation of stable ferrihydrites, require high iron to arsenic ratios and the need to limit the arsenic concentration in the final effluent. As a result, arsenic waste streams are often voluminous and must either be discharged to tailing ponds or treated as hazardous waste.

A process has recently been proposed by Adham et al. for direct fixation of arsenic as a stable arsenate from a de-arsenifying roast (Two-Stage Fluid Bed Reactor for Arsenic Removal and Fixation—COM Proceedings, 2014). This process uses a two-stage high-temperature fluid bed reactor, in which the first stage removes the arsenic through a neutral roast, by volatilization as mostly sulfide species. The second stage captures the arsenic from the gas phase through oxidative fixation, as a stable iron arsenate, by reaction with an appropriate iron source.

There remains a need for simpler processes and reactors for fixation of arsenic into stable forms which provide lower equipment costs and/or lower operating costs than known processes and reactors.

SUMMARY

In one embodiment, there is provided a process for arsenic fixation. The process comprises: (a) providing a reactor having an internal space; (b) providing a first gas stream in said internal space, wherein the first gas stream comprises oxygen and an iron-containing particulate material; (c) providing a second gas stream in said internal space, wherein the second gas stream comprises one or more arsenic species; (d) mixing the first gas stream and the second gas stream in said internal space to produce a combined gas stream; (e) reacting the one or more volatile arsenic compounds, the iron-containing particulate material and the oxygen in the combined gas stream to produce solid iron arsenates in the combined gas stream; and (f) separating the solid iron arsenates from the combined gas stream.

In another embodiment, there is provided a reactor for arsenic fixation. The reactor comprises: (a) an internal space having a first end and a second end, with a gas flow direction being defined from the first end to the second end; (b) a first inlet adapted for feeding a gaseous oxidant mixture into the internal space, wherein the first inlet is located proximate to the first end; (c) optionally a second inlet adapted for feeding an iron-containing particulate material into the internal space, wherein the second inlet is located downstream of the first inlet in the gas flow direction; (d) a third inlet adapted for feeding a second gas stream into the internal space, wherein the third inlet is located downstream of the first inlet and the second inlet, where one is provided, in the gas flow direction; (e) a preliminary reaction zone located downstream of the first inlet, the second inlet where one is provided, and the third inlet.

BRIEF DESCRIPTION OF THE DRAWINGS

The invention will now be described, by way of example only, with reference to the attached drawings, in which.

DETAILED DESCRIPTION

Figure 1:
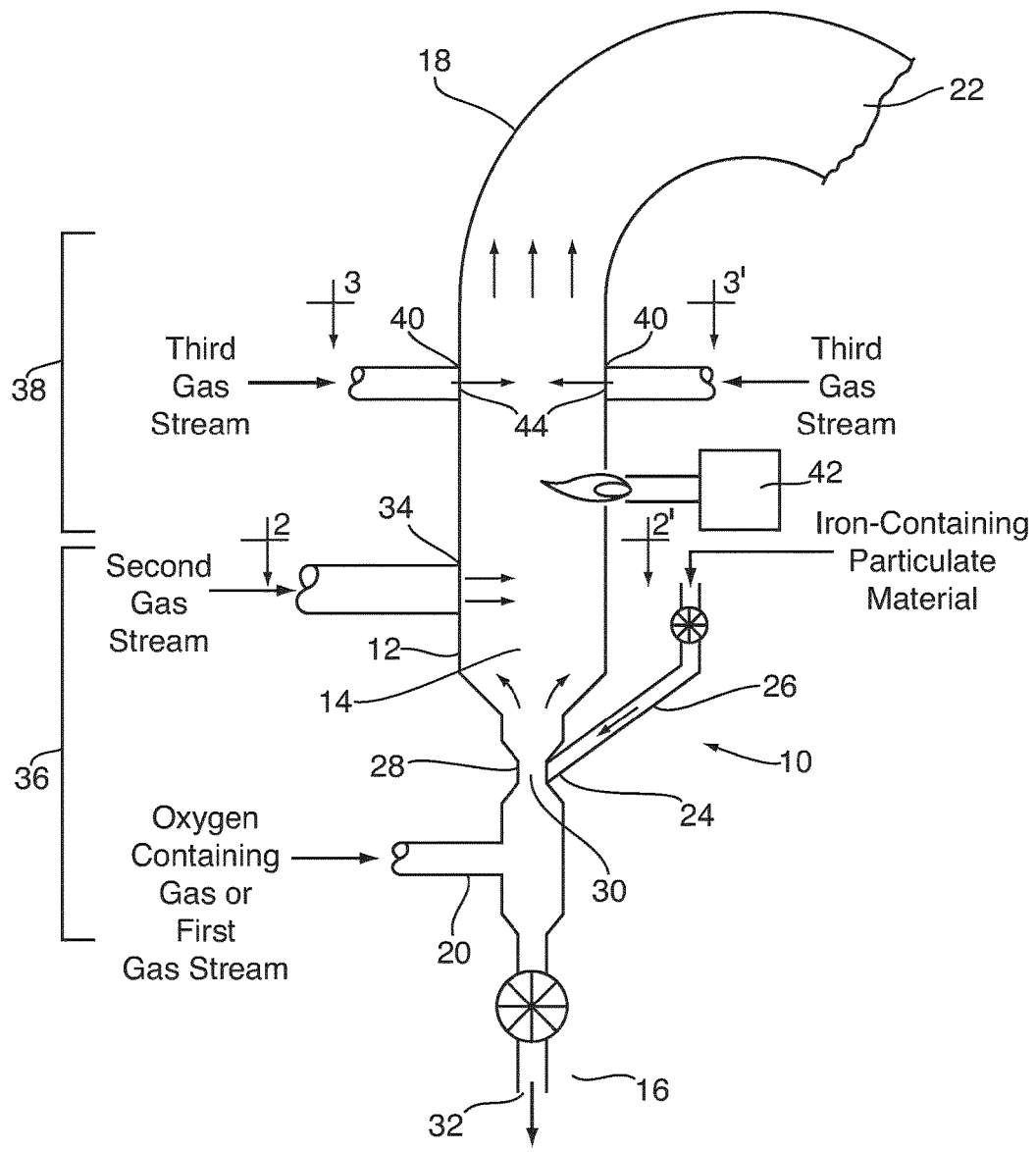
FIG. 1 is a schematic side view of a reactor according to an embodiment described herein.
Figure 2:
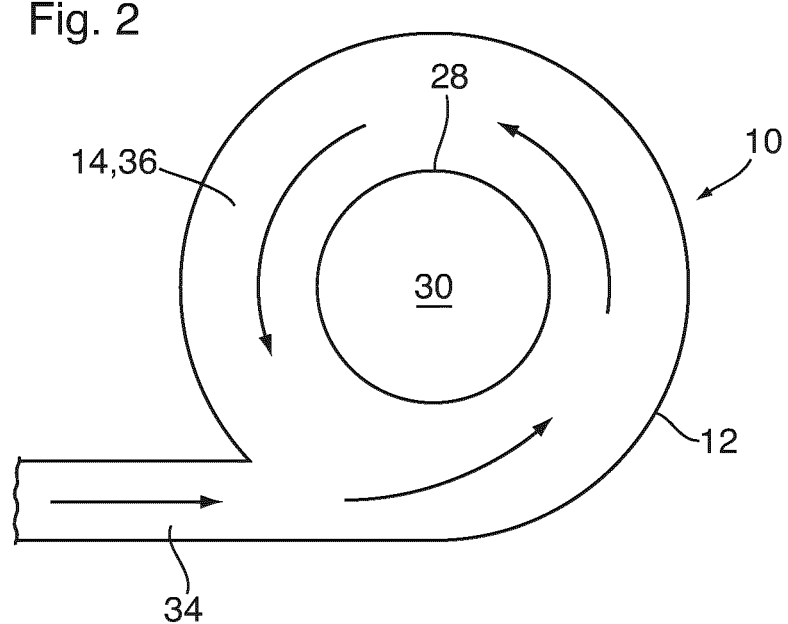
FIG. 2 is a cross-section along line 2-2' of FIG. 1.
Figure 3:
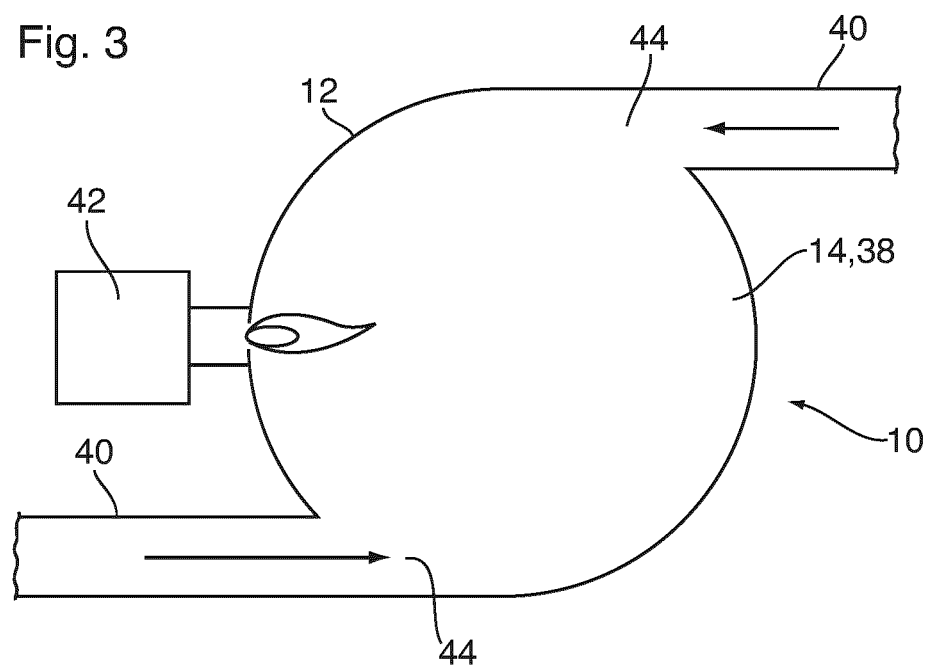
FIG. 3 is a cross-section along line 3-3' of FIG. 1.

FIGS. 1 to 3 illustrate a reactor 10 according to a first embodiment. Reactor 10 comprises an outer side wall 12 having a generally elongate, tubular form, and which may be cylindrically shaped along at least a portion of its length. Reactor 10 is sometimes referred to herein as a "flash tube reactor".

Reactor 10 has an internal space 14 enclosed by side wall 12. As will be further described below, the internal space 14 is divided into several zones and has a first end 16 and a second end 18, with a gas flow direction being defined from the first end 16 to the second end 18. In the present embodiment the reactor 10 is vertically oriented along at least a portion of its length, such that at least a portion of the internal space 14 is vertically oriented, and the gas flow direction is vertical, with the second end 18 being located above the first end 16 (i.e. downstream in the gas flow direction).

The reactor 10 has a first inlet 20 which in the present embodiment is located proximate to the first end 16. The first inlet 20 is adapted for feeding a gaseous oxidant mixture into the internal space 14. The gaseous oxidant mixture includes an oxidant which is molecular oxygen (referred to herein as "oxygen"), and may typically comprise air at ambient pressure and temperature. However, the gaseous oxidant mixture may instead comprise an oxygen-containing gas other than air. In some embodiments, the gaseous oxidant mixture which enters the internal space 14 through the first inlet will further comprise an iron-containing particulate material, and a gaseous oxidant mixture including this particulate material is referred to herein as the "first gas stream" or the "primary gas stream", and is further described below. The composition and/or flow rate of the gaseous oxidant mixture fed through first inlet 20 is variable, and depends on the gas composition of the arsenic-containing gas stream being fed to reactor 10.

The gaseous oxidant mixture fed into internal space 14 through first inlet 20 forms the first gas stream or primary gas stream which flows through the internal space 14 from the first inlet 20 toward an outlet 22 of reactor 10. The outlet 22 of reactor 10 is shown as being located proximate to the second end 18 of reactor 10, however, it will be appreciated that the reactor 10 may include further horizontal and/or vertical sections between the first inlet 20 and the outlet 22. Therefore, the gas flow direction is vertical from the first end 16 to the second end 18 of internal space 14, but the gas flow direction from the second end 18 of internal space 14 to the outlet 22 of reactor 10 is not necessarily vertical, and may include non-vertical sections. It will be appreciated that FIG. 1 may show only a portion of the flow path followed by the first gas stream from the first inlet 20 to the outlet 22.

The first gas stream comprises an oxidant, typically oxygen, and an iron-containing particulate material, and is provided in the internal space 14 of reactor 10. In some embodiments, the gaseous oxidant mixture comprises the first gas stream, and comprises a mixture of an oxygen-containing gas such as air, with the particulate material suspended therein, the first gas stream being formed outside the reactor 10 by pre-mixing the oxygen-containing gas and the iron-containing particulate material. According to these embodiments, the first gas stream which is formed outside the reactor 10 is fed into the internal space 14 of the reactor 10 through the first inlet 20.

In other embodiments the gaseous oxidant mixture fed into internal space 14 through first inlet 20 comprises an oxygen-containing gas such as air, which is mixed with the iron-containing particulate material inside the internal space 14 of reactor 10, i.e. such that the first gas stream is formed inside the internal space 14. An example of such an embodiment is illustrated in FIG. 1 and is now described below.

In the embodiment shown in FIG. 1, the reactor 10 further comprises a second inlet 24 adapted for feeding the iron-containing particulate material into the internal space 14, to mix with the oxygen-containing gas to form the first gas stream flowing upwardly through the internal space 14. As shown, the second inlet 24 is located downstream of (i.e. above) the first inlet 20 in the gas flow direction.

The iron-containing particulate material may be in the form of a finely divided solid material, which may be fed to the second inlet 24 through a feed pipe 26. The feed pipe 26 may be angled downwardly toward the second inlet 24 as shown in FIG. 1, such that the iron-containing particulate material is fed to reactor 10 by gravity.

The composition of the iron-containing particulate material is highly variable. For example, the iron-containing particulate material may comprise an iron-bearing mineral or material which in the presence of oxygen and arsenic may at least partially react to form an iron arsenate-containing compound. Examples of suitable iron-bearing minerals include hematite, magnetite, goethite, pyrite and pyrrhotite. The iron-containing particulate material may include elemental iron or iron (II) and/or iron (III) oxides in other forms. The iron-containing particulate material may comprise by-products or waste products of other processes, and/or may include a portion of the solids recovered downstream of reactor 10 in the present process.

The reactor 10 may include an arrangement to promote mixing of the iron-containing particulate material and the oxygen-containing gas to form the first gas stream. For example, the reactor 10 according to the present embodiment includes a venturi arrangement 28 having a throat 30 which is narrower than portions of the internal space 14 immediately upstream and downstream of the venturi arrangement 28. As shown in FIG. 1, the second inlet 24 may be located within or proximate to the throat 30 of the venturi arrangement 28. For example, as shown in FIG. 1, the second inlet 24 is located proximate to the throat 30 of the venturi arrangement 28, being located immediately downstream thereof in the gas flow direction.

Once the iron-containing particulate material is mixed with the oxygen-containing gas, the resulting first gas stream flows upwardly through internal space 14. Any particles of the particulate material which are too heavy and/or coarse to be entrained in the first gas stream will fall down toward the first end 16 of reactor 10, where they are withdrawn from reactor 10 through drop out opening 32.

The present process further comprises providing a second gas stream in the internal space 14. To accomplish this, the reactor 10 further comprises a third inlet 34 adapted for feeding an arsenic-containing second gas stream into the internal space 14, and more specifically into the first gas stream flowing upwardly through the internal space 14. As shown, the third inlet 34 is located downstream of (i.e. above) the first inlet 20. Also, in the present embodiment, the third inlet 34 is located downstream of (above) the second inlet 24, such that first gas stream will be formed by mixing the oxygen-containing gas with the iron-containing particulate material before it is mixed with the arsenic-containing second gas stream. The combination of the first and second gas streams and the iron-containing particulate material is sometimes referred to herein as the "combined gas stream".

The arsenic-containing second gas stream includes one or more arsenic species selected from the group comprising arsenic oxide, arsenic sulfide and elemental arsenic. The majority of these arsenic species will be in gaseous form, although the second gas stream may contain some entrained liquid or solid arsenic species, and may also contain various concentrations of other species (inert and reactive), depending on the origin of the second gas stream. The second gas stream is typically maintained at a temperature sufficient to maintain the arsenic species in a predominantly gaseous state. For example, the second gas stream may be maintained at a temperature of from about 400° C. to about 800° C. as it is fed to the internal space 14 through the third inlet 34 in order to maintain volatile arsenic species such as arsenic oxides and arsenic sulfides in the gaseous state.

The second gas stream may originate from a number of sources. For example, the second gas stream may be the product of a dearsenifying reducing/neutral roast of an arsenic-bearing mineral in a process for producing gold, copper or nickel.

In order to provide thorough mixing between the second gas stream and the first gas stream containing the entrained particulate material, the arsenic-containing second gas stream may be fed into the internal space 14 in the form of a swirling, tangential flow through the third inlet 34, which is substantially perpendicular to the (vertical) gas flow direction through the internal space 14. To achieve this tangential, swirling flow, the third inlet 34 may comprise one or more tangentially arranged inlet openings to feed the second gas stream into the internal space 14 in the form of a swirling, tangential flow.

In addition, the third inlet 34 may be arranged to direct the second gas stream in a direction which is substantially perpendicular to a direction of flow of the first gas stream through the internal space 14. For example, in the illustrated embodiment where the flow of the first gas stream is vertical, the second gas stream may be introduced into the internal space 14 in a predominantly horizontal direction.

The cross-section of FIG. 2 shows the swirling flow of the second gas stream in the radially outer areas of the internal space 14, and mixing with the vertically flowing first gas stream in the radially inner areas of the internal space 14, to form the combined gas stream.

As shown in FIG. 1, the introduction and mixing of the first gas stream containing the iron-containing particulate material, and the arsenic-containing second gas stream takes place in the vertically-oriented portion of the internal space 14. This portion of the internal space 14 in which the mixing takes place is identified in FIG. 1 as mixing zone 36.

Where the iron-containing particulate material is in the form of an aqueous slurry, it may be necessary to introduce the slurry into the mixing zone 36 above the venturi arrangement 28.

Once the first and second gas streams are mixed to form the combined gas stream, the volatile arsenic compounds of the second gas stream are brought into contact with the entrained iron-containing particulate material and oxygen of the first gas stream, resulting in reaction of the arsenic compounds to produce solid iron arsenates having the general formula $FeAsO_4$.

In the illustrated embodiment the reactor 10 includes a preliminary reaction zone 38 located immediately downstream of (above) the mixing zone 36, and through which the combined gas stream flows after being formed by mixing the first and the second gas streams. As shown in FIG. 1, the preliminary reaction zone 38 may be located in the vertical portion of the internal space 14, and is located downstream of the first inlet 20, the second inlet 24 and the third inlet 34 in the gas flow direction, and is located in the vertically oriented portion of the internal space 14.

In the preliminary reaction zone 38, the oxygen from the first gas stream reacts with and at least partially oxidizes the arsenic species from the second gas stream to produce arsenic oxides, including $As_4O_6$; and react with and oxidize the iron-containing particulate material from the second gas stream, and/or other gaseous species present in the combined gas stream. At least some of the iron arsenates may also form in the preliminary reaction zone 38.

The reactor 10 may further comprise a fourth inlet 40 adapted for feeding a third gas stream into the preliminary reaction zone 38 to mix with and become incorporated in the combined gas stream flowing through and undergoing reaction in the preliminary reaction zone 38. The fourth inlet 40 is located in the preliminary reaction zone 38 and is located downstream of the first inlet 20, the second inlet 24 and the third inlet 34 in the gas flow direction. The third gas stream comprises an oxygen-containing gas, and will typically comprise air at ambient pressure and temperature, but may instead comprise another oxidant. This secondary oxidant stream is introduced in order to ensure complete combustion and reaction by promoting the oxidizing environment required to ensure ferric arsenate formation.

The preliminary reaction zone 38 and the combined gas stream flowing therethrough are maintained at a temperature sufficient to ensure ignition and reaction, and to promote combustion stability within the preliminary reaction zone 38. The reaction temperature is a function of the compositions and flow rates of the first, second and third gas streams. Generally the preliminary reaction zone 38 is maintained at a temperature of from about 500° C. to about 1,000° C.

Temperature control within the preliminary reaction zone 38 can be provided by a heating arrangement 42, such as a burner, in which natural gas may be combusted with air. Additional temperature control (cooling) can be provided by water spray (not shown) into the preliminary reaction zone 38.

As with the second gas stream, the oxygen-containing third gas stream may be fed into the preliminary reaction zone 38 in the form of a swirling, tangential flow through the fourth inlet 40. To achieve this tangential, swirling flow, the fourth inlet 40 may comprise one or more tangentially arranged inlet openings to feed the third gas stream into the preliminary reaction zone 38 in the form of a swirling, tangential flow. The side view of FIG. 1 and the cross-section of FIG. 3 show two tangential inlet openings 44, however, it will be appreciated that the third gas inlet may instead comprise a single opening 44 or greater than two openings 44.

In addition, the fourth inlet 40 may be arranged to direct the third gas stream in a direction which is substantially perpendicular (i.e. horizontal) to a direction of flow of the combined gas stream through the preliminary reaction zone 38.

The reactor 10 may include additional vertical and horizontal sections, as well 90 degree and/or 180 degree bends, to provide additional residence time for completion of the reaction. Bends also promote gas-solids mixing and permit the reactor have a compact size.

The solid iron arsenates are entrained in the combined gas stream flowing through the preliminary reaction zone 38 and any portions of the reactor 10 located downstream of the preliminary reaction zone 38, and may be recovered downstream of reactor 10 using any number of standard gas-solid separation techniques, such as gas cooling and/or de-dusting.

Thus, the embodiment described above provides direct fixation of arsenic species in a gas stream to solid, stable iron arsenates. The construction of the reactor 10 in the form of a flash tube reactor provides a number of benefits over known processes and reactors, including two-stage high-temperature fluid bed reactors. For example, the flash tube reactor described herein provides has a lower pressure drop than a fluidized bed of solid particles, and a smaller volume than a fluidized bed reactor. In addition, the flash tube reactor avoids potential issues with plugging of tuyeres in a fluid bed reactor by condensation of arsenic species from the arsenic-containing feed gas.

Figure 4:
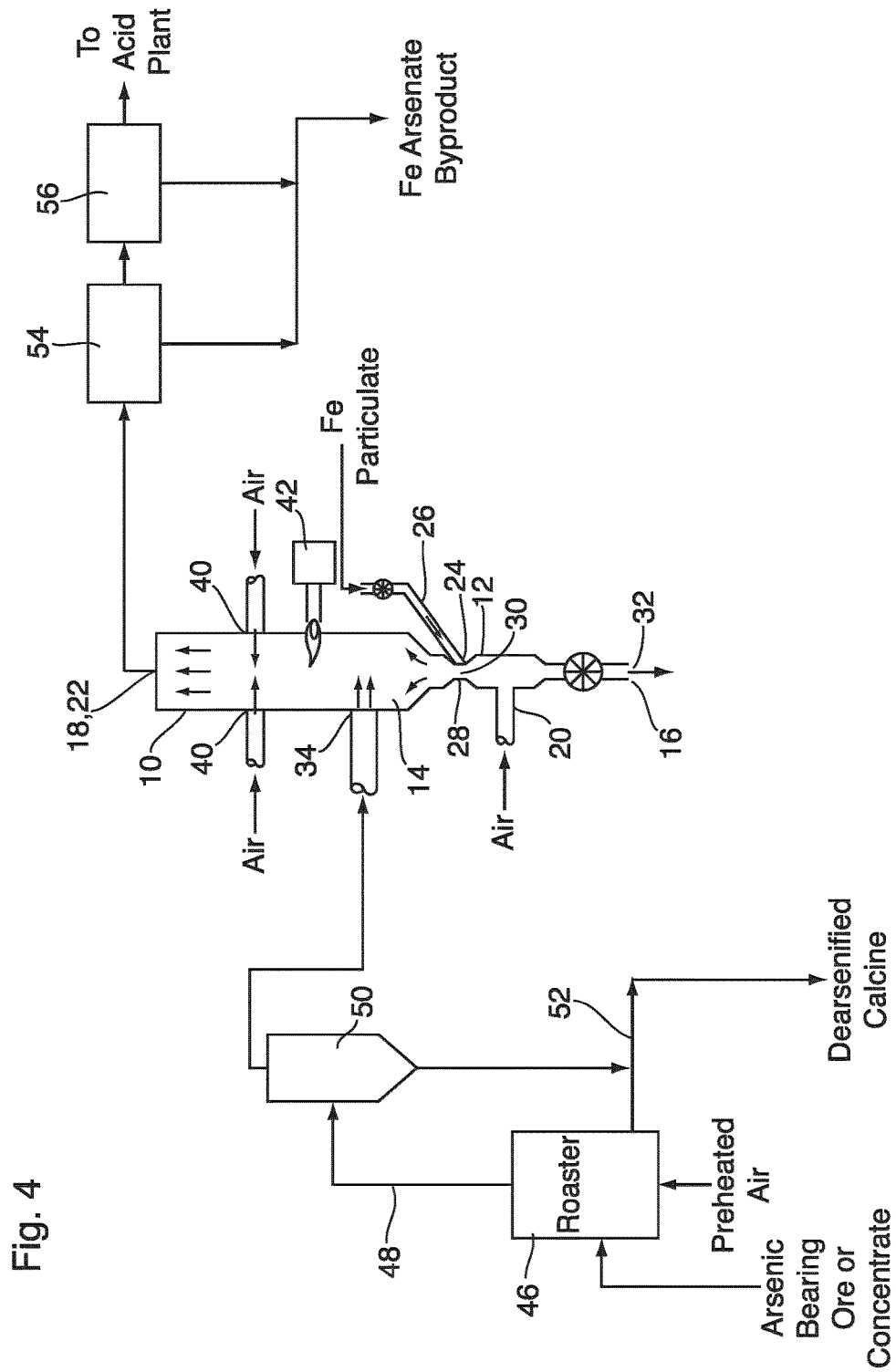
FIG. 4 is a flow diagram for a process according to an embodiment described herein.

FIG. 4 illustrates process for fixation of arsenic, which integrates a reactor 10 as described above. According to this process, an arsenic-bearing ore or concentrate is fed to a roaster 46, along with preheated air. The roasting process results in separation of the arsenic from the ore or concentrate as volatile arsenic species which are removed from the roaster 46 in the off-gas 48. The dearsenified calcine is removed from roaster 46 for further processing to recover metal values therefrom.

The off-gas 48 is fed to a cyclone 50 in which any entrained solids are separated and combined with the dearsenified calcine at 52. The arsenic-containing off-gas is then fed to a reactor 10 in the form of the second gas stream, as described above, and is fed into the internal space 14 where it is mixed with the first gas stream and optionally the third gas stream, as described above.

The resulting solid iron arsenates are entrained in the gases flowing upwardly through the reactor 10, and exit the outlet 22 of reactor 10. Next, the arsenate-containing gases may be subjected to gas cooling at 54 and de-dusting at 56, thereby separating the solid iron arsenate by-product from the gas fraction. The arsenates can be disposed of as non-hazardous waste and the gases may be subjected to further treatment in an acid plant.

Although the invention has been described with reference to certain specific embodiments, it is not limited thereto. Rather, the invention includes all embodiments which may fall within the scope of the following claims.

What is claimed is:

1. A process for arsenic fixation, comprising:
   (a) providing a reactor having an internal space;
   (b) providing a first gas stream in said internal space, wherein the first gas stream comprises oxygen and an iron-containing particulate material;
   (c) providing a second gas stream in said internal space, wherein the second gas stream comprises one or more arsenic species;
   (d) mixing the first gas stream and the second gas stream in said internal space to produce a combined gas stream;
   (e) reacting the one or more arsenic species, the iron-containing particulate material and the oxygen in the combined gas stream to produce solid iron arsenates in the combined gas stream; and
   (f) separating the solid iron arsenates from the combined gas stream.

2. The process according to claim 1, wherein the internal space of the reactor has a first end and a second end, with a gas flow direction being defined from the first end to the second end.

3. The process according to claim 2, wherein at least a portion of the internal space is oriented vertically, wherein the gas flow direction is vertical, and wherein the mixing of the first gas stream with the second gas stream takes place within the vertically oriented portion of the internal space.

4. The process according to claim 1, wherein the iron-containing particulate material includes one or more iron-bearing minerals, elemental iron, iron (II) oxide and/or iron (III) oxide.

5. The process according to claim 2, wherein the first gas stream comprises an oxygen-containing gas in which the iron-containing particulate material is suspended.

6. The process according to claim 5, further comprising the step of forming the first gas stream by pre-mixing the oxygen-containing gas and the iron-containing particulate material outside the reactor; and wherein said step (b) comprises feeding the first gas stream into the internal space of the reactor through a first inlet.

7. The process according to claim 5, wherein said step (b) comprises:
   (i) feeding the oxygen-containing gas into the internal space of the reactor through a first inlet;
   (ii) feeding the iron-containing particulate material into the internal space of the reactor through a second inlet; and
   (iii) mixing the oxygen-containing gas and the iron-containing particulate material inside the internal space of the reactor.

8. The process according to claim 7, wherein the second inlet is located downstream of the first inlet in the gas flow direction.

9. The process according to claim 7, wherein the reactor further comprises a venturi arrangement having a throat which forms part of the internal space, and wherein the second inlet is located at or downstream of the throat of the venturi arrangement in the gas flow direction.

10. The process according to claim 5, wherein the oxygen-containing gas is air.

11. The process according to claim 1, wherein the one or more arsenic species are selected from the group comprising arsenic oxide, arsenic sulfide and elemental arsenic.

12. The process according to claim 7, wherein said step (c) comprises feeding the second gas stream into the internal space of the reactor through a third inlet which is located downstream of the first inlet and the second inlet.

13. The process according to claim 12, wherein the second gas stream is at a temperature of from about 400° C. to about 800° C. as it is fed into the internal space through the third inlet.

14. The process according to claim 12, wherein the second gas stream is fed into the internal space as a swirling, tangential flow from the third inlet; and
   wherein the swirling, tangential flow of the second gas stream is substantially perpendicular to the gas flow direction.

15. The process according to claim 1, wherein the internal space of the reactor includes a preliminary reaction zone through which the combined gas stream flows after being formed by mixing the first and second gas streams, and wherein said step (e) at least partially takes place in the preliminary reaction zone.

16. The process according to claim 15, further comprising the step of adding heat to the preliminary reaction zone to maintain the preliminary reaction zone and the combined gas stream flowing through the preliminary reaction zone at a temperature of from about 500° C. to about 1,000° C.

17. The process according to claim 15, further comprising the step of feeding a third gas stream into the preliminary reaction zone to mix with the combined gas stream flowing through the preliminary reaction zone, wherein the third gas stream comprises an oxygen-containing gas.

18. The process according to claim 17, wherein the third gas stream is fed into the preliminary reaction zone as a swirling, tangential flow from the fourth gas inlet.

* * * * *